United States Patent [19]

Chorvat

[11] 4,193,930

[45] Mar. 18, 1980

[54] 25-ALKYL-3β-HYDROXYCHOLEST-5-EN-7-ONES AND ESTERS THEREOF

[75] Inventor: Robert J. Chorvat, Arlington Heights, Ill.

[73] Assignee: G. D. Searle & Co., Skokie, Ill.

[21] Appl. No.: 928,664

[22] Filed: Jul. 28, 1978

Related U.S. Application Data

[63] Continuation-in-part of Ser. No. 828,385, Aug. 29, 1977.

[51] Int. Cl.$^2$ ................................................. C07J 9/00
[52] U.S. Cl. ................................................. 260/397.2
[58] Field of Search ..................................... 260/397.2

[56] References Cited

U.S. PATENT DOCUMENTS 4,006,172   2/1977   Salmond ........................... 260/397.2

OTHER PUBLICATIONS

Mol. Cryst. Liq. Cryst., 1971, p. 255.
"Journal Biol. Chemistry", vol. 248, No. 24, (1973), pp. 8408–8417, article by Kandutsch et al.
"Journal Biol. Chemistry", vol. 249, No. 22, (1974), pp. 7306–7314, article by Brown et al.
"Journal Chem. Res.", (1977), p. 2522.

Primary Examiner—Elbert L. Roberts
Attorney, Agent, or Firm—James R. Henes; John M. Brown

[57] ABSTRACT

25-Alkyl-3β-hydroxycholest-5-en-7-ones and esters thereof adapted to lower serum cholesterol and inhibit the activity of 3-hydroxy-3-methylglutaryl coenzyme A reductase are disclosed.

2 Claims, No Drawings

25-ALKYL-3β-HYDROXYCHOLEST-5-EN-7-ONES AND ESTERS THEREOF

The application for Letters Patent securing the invention herein described and claimed is a continuation-in-part of Applicant's copending application, Ser. No. 828,385 filed Aug. 29, 1977.

This invention relates to 25-alkyl-3β-hydroxycholest-5-en-7-ones and esters thereof. More particularly, this invention provides new, useful, and unobvious chemical compounds of the formula

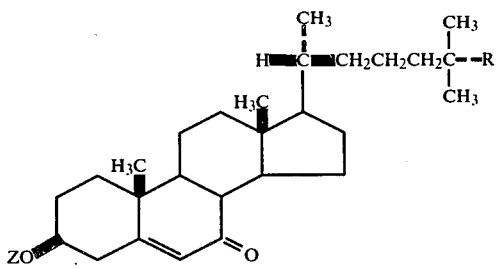

wherein R represents alkyl and Z represents hydrogen or an esterifying moiety such as 1-oxoalkyl frequently but not invariably Ω-substituted by carboxyl.

Among the alkyls represented by R, those containing fewer than 5 carbons are preferred, namely, methyl, ethyl, 1-methylethyl, 1,1-dimethylethyl, propyl, 1-methylpropyl, 2-methylpropyl, and butyl.

Among the esterifying moieties represented by Z, those of the formula

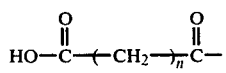

wherein n represents a positive integer less than 4 are preferred, namely, 2-carboxy-1-oxoethyl, 3-carboxy-1-oxopropyl, and 4-carboxy-1-oxobutyl.

The compounds to which this invention relates are useful by reason of their valuable pharmacological properties. Thus, for examle, they lower serum cholesterol levels and inhibit the activity of 3-hydroxy-3-methylglutaryl coenzyme A (HMG CoA) reductase, an enzyme which controls the rate at which cholesterol is synthesized in mammalian liver (one of the two principal sources of serum cholesterol). The innovative significance of compounds adapted to inhibit sterol biosynthesis in individuals predisposed to familial type II hypercholesterolemia (WHO classification) is widely recognized. See, for example Breslow et al., Biochem. et Biophys. Acta, 398, 10 (1975); Betteridge et al., Brit. Med. J., 4, 500 (1975); and Brown et al., J. Biol. Chem., 249, 7306 (1974).

The cholesterol-lowering utility of the instant compounds is evident from results of the following test procedure: Male Charles River COBS-CD rats, initially weighing approximately 200 g apiece, are housed in pairs and maintained on a standard rat diet plus water ad libitum. To each of a group of 6 such animals, daily for 5 days 5 mg/kg of compound dissolved or suspended in 0.2 ml of propylene glycol is intragastrically administered. Approximately 2 hr. after compound administration on the 5th day, the animals are anesthetized and approximately 3 ml of blood is removed from the abdominal aorta of each animal. A second group of 6 animals concurrently and identically treated except that no compound is administered, serves as controls. The blood samples are analyzed for serum cholesterol via the Libermann-Burchard reaction, substantially as described by Levine et al. in "Automation in analytical chemistry," v. 1, pp. 25–28, 1968, Mediad, White Plains, N.Y. A compound qualifies as effective in this test if the mean mg percent cholesterol level in the group to which it is administered is significantly lowered ($P \leq 0.05$, Student's t), relative to the corresponding control level. One of the preferred embodiments of this invention, 3β-hydroxy-25-methylcholest-5-en-7-one, was found to lower serum cholesterol 14% when thus tested.

The HMG CoA reductase-inhibiting utility of the instant compounds is evident from results of the following test procedure: Male Charles River CD rats, initially weighing 180–250 g apiece, are randomized in groups of 6, housed in a reverse light cycle (12:12) room, and maintained therein on a standard rat diet plus water ad libitum. To each animal in a group, after at least 3 but not more than 6 days, 5 mg/kg of 20,25-diazacholesterol dissolved in 0.2 ml of physiological saline containing 0.1% of polyoxyethylene sorbitan monooleate (Tween 80) is intragastrically administered on each of 7 consecutive days, during the last 4 of which test compound is concurrently administered at a pre-selected daily dose (commonly 5 mg/kg intragastrically). Controls are provided by a second group of animals identically treated except that the test compound is omitted. Within 2–4 hr. after treatment is completed, and 5–7 hr. into the dark cycle, the animals are anesthetized with 1,1'-oxybisethane and thereupon killed. Livers are quickly removed, washed with a chilled homogenization medium (preparable by dissolving 102.7 g of sucrose, 3.8 g of sodium edetate, and 0.8 g of dithiothreitol in water q.s. 1000 ml), blotted dry, weighed, and homogenized (using 2 ml of the aforesaid chilled medium for each g of liver). The homogenates are centrifuged at 4° C. and 15,000×g for 15 min., whereupon the supernatants are separated and centrifuged at 4° C. and 100,000×g for 60 min. The resultant supernatants are discarded and the residues suspended in half the volume of homogenization medium previously employed (i.e., 1 ml for each g of residue). HMG CoA reductase activity is assayed substantially in accordance with procedures described by L. W. White et al. in Biochemistry, 9, 2713 (1970); M. S. Brown et al. in J. Biol. Chem., 248, 4731 (1973); and P. A. Edwards et al. in Biochim. Biophys. Acta, 409, 39 (1975). Protein is determined by the method of O. H. Lowry et al., J. Biol. Chem., 193, 265 (1951). The data obtained are converted to specific activity (nmol/20min./mg) for each animal, from which group mean(s) and percent change, relative to controls, are calculated. A statistically significant response ($P \leq 0.05$) is the criterion for HMG CoA reductase inhibition/stimulation. 3β-Hydroxy-25-methylcholest-5-en-7-one was found to inhibit enzyme activity in this test by 54, 31, 26, and 4% at 50, 10, 5, and 1 mg/kg, respectively, and to stimulate the activity by 15% at 0.5 mg/kg when administered intragastrically. These results are statistically significant ($P \leq 0.05$) at the 5, 10, and 50 mg/kg dose levels and the more remarkable because 3β-hydroxycholest-5-en-7-one, a prior art compound differing therefrom solely by the absence of the 25-methyl therein, stimulated HMG CoA redustase activity at 30 mg/kg both intragastrically and subcutaneously (by 4 and 27%, respectively, the latter being a statistically significant response) under the same test conditions.

The characterizing pharmacological responses to one of the embodiments of this invention hereinabove set forth are specified merely for purposes of illustration, and are accordingly not to be construed as either delimiting or exclusionary.

For therapeutic reasons, the compounds of this invention are ordinarily combined with one or more adjuvants appropriate to the indicated route of administration. If per os, they may be admixed with lactose, sucrose, starch powder, cellulose esters of alkanoic acids, cellulose alkyl ethers, talc, stearic acid, magnesium stearate, magnesium oxide, sodium and calcium salts of phosphoric and sulfuric acids, gelatin, acacia, sodium alginate, polyvinylpyrrolidone, and/or polyvinyl alcohol, and thus tableted or encapsulated for convenient administration; alternatively, they may be dissolved or suspended in water or a comparably innocuous liquid. Parenteral administration may be effected via sterile fluid admixture with water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art; see, for example, F. W. Martin et al., "Remington's Pharmaceutical Sciences," 14th Ed., Merck Publishing Company, Eaton, Pa., 1965.

Appropriate dosages, in any given instance, of course depend upon the nature and severity of the condition treated, the route of administration, and the species of mammal involved, including its size and any individual idiosyncrasies which obtain.

Preparation of compounds of this invention proceeds variously as follows: 3α,5-Cyclo-6β-methoxy-23,24-dinor-5α-cholan-20-al [Steroids, 15, 113 (1970)] is contacted in a very cold mixture of tetrahydrofuran and 1,1'-oxybisethane with a phosphorane of the formula

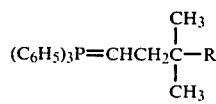

[formed in situ by contacting an appropriate (3,3-dimethylalkyl)triphenylphosphonium halide with phenyllithium at room temperature], whereupon aqueous ammonium chloride is added to the mixture. The resultant unsaturated i-steroid

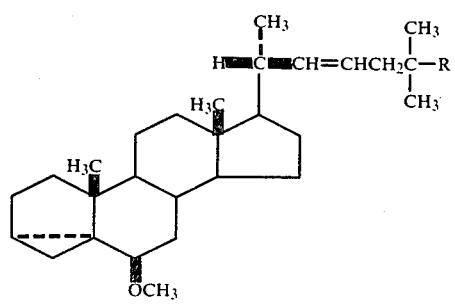

is hydrogenated at low pressure in ethanol, using palladium-on-charcoal as catalyst; and the i-steroid which eventuates

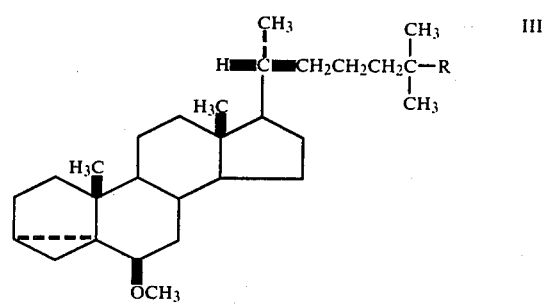

is rearranged by heating with an alkanoic acid, giving rise to the corresponding ester

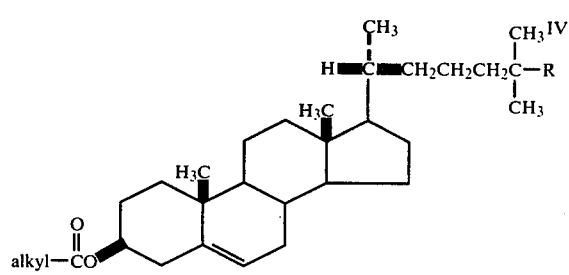

contacting an ester of formula IV with chromium oxide and pyridine in dichloromethane under nitrogen affords the corresponding 7-one of the invention, having the formula Heating an ester of formula V with sodium bicarbonate in aqueous ethanol affords the corresponding 3β-hydroxy compound of the invention, having the formula Heating a compound of formula VI in pyridine with a methyl Ω-chloro-Ω-oxoalkanoate and heating the mixed ester thus obtained

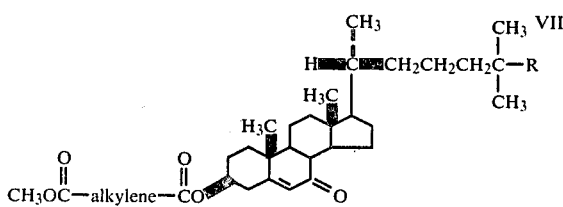

with lithium iodide in pyridine, 2,6-dimethylpyridine, or 2,4,6-trimethylpyridine affords an ester of the invention having the formula

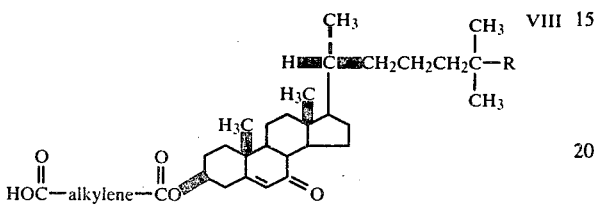

As an exception to the foregoing procedure, a compound of formula VIII wherein the esterifying moiety is 3-carboxy-1-oxopropyl is preferably prepared by heating a compound of formula VI with butanedioic acid anhydride in pyridine.

In each of formulas I through VIII hereinbefore, R represents alkyl preferably containing fewer than 5 carbons.

The following examples describe in detail compounds illustrative of the present invention and methods which have been devised for their preparation. It will be apparent to those skilled in the art that many modifications, both of materials and of methods, may be practiced without departing from the purpose and intent of this disclosure. Throughout the examples hereinafter set forth, temperatures are given in degrees centigrade and relative amounts of materials in parts by weight, except as otherwise noted.

EXAMPLE 1

A. To a solution of 39 parts of (3,3-dimethylbutyl)-triphenylphosphonium iodide in 335 parts of tetrahydrofuran is added, with stirring during 5 min. under a nitrogen atmosphere, a solution of approximately 7 parts of phenyllithium in a mixture of 30 parts of benzene with 10 parts of 1,1'-oxybisethane. Stirring of the resultant orange-red solution is continued for 15 min., whereupon the solution is cooled to −70° and a solution of 20 parts of 3α,5-cyclo-6β-methoxy-23,24-dinor-5α-cholan-20-al [Steroids, 15, 113 (1970)] in 110 parts of tetrahydrofuran then stirred in during 5 min. Stirring at − 70° is continued for 30 min. longer, at which point the reaction mixture is allowed to warm to room temperature and thereupon partitioned between an aqueous saturated solution of ammonium chloride and 1,1'-oxybisethane. The 1,1'-oxybisethane phase is separated, washed with an aqueous saturated solution of sodium chloride, dried over anhydrous sodium sulfate, and stripped of solvent by vacuum distillation. The residual oil is dissolved in a minimum volume of pentane. The pentane solution is stirred at room temperature while a precipitate forms. The precipitate is removed by filtration; and the filtrate is concentrated by distillation to one-half volume, whereupon the precipitate which forms in the distilland is removed by filtration and the filtrate thus obtained is stripped of solvent by vacuum distillation. The residual oil is 3α,5-cyclo-6β-methoxy-25-methyl-5α-cholest-22-ene.

B. To a solution of 5 parts 3α,5-cyclo-6β-methoxy-25-methyl-5α-cholest-22-ene in 160 parts of ethanol is added 5 parts of 5% palladium-on-carbon. The resultant mixture is hydrogenated at approximately 500 Nm$^{-2}$ until hydrogen uptake indicates that saturation of the steroidal double bond is complete. Catalyst is thereupon removed by filtration, and the filtrate is stripped of solvent by vacuum distillation. The residual oil is 3α,5-cyclo-6β-methoxy-25-methyl-5α-cholestane.

C. A solution of 4 parts of 3α,5-cyclo-6β-methoxy-25-methyl-5α-cholestane in 30 parts of glacial acetic acid is heated at 90°–95° for 2 hrs., then cooled to 65° and diluted thereat with 30 parts of hot methanol. A precipitate forms in the resultant solution as it cools. The precipitate is isolated by filtration and recrystallized from a mixture of 1,1'-oxybisethane and methanol to give 25-methylcholest-5-en-3β-ol 3-acetate melting at approximately 152°–153°.

D. To a mixture of approximately 8 parts of pyridine with 95 parts of dichloromethane in a nitrogen atmosphere is added, portion-wise with stirring at room temperature, 5 parts of chromic oxide. The resultant burgundy mixture is stirred for ½ hour, whereupon a solution of 1 part of 25-methylcholest-5-en-3β-ol 3-acetate in 7 parts of dichloromethane is introduced and stirring at room temperature continued thereafter for 16 hours. Approximately 3 volumes of 1,1'-oxybisethane are then mixed in and insoluble solids allowed to settle out. The supernatant solution is separated therefrom by decantation and filtered through diatomaceous earth. The filtrate is consecutively washed with 5% hydrochloric acid, aqueous 5% sodium bicarbonate, and an aqueous saturated solution of sodium chloride; dried over anhydrous sodium sulfate; and stripped of solvent by vacuum distillation. The residual oil is crystallized from aqueous ethanol, affording 3β-hydroxy-25-methylcholest-5-en-7-one 3-acetate melting at 183°–186°, and having the formula

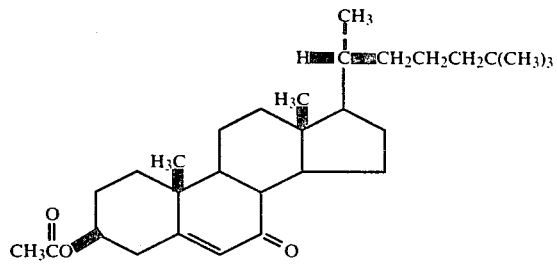

EXAMPLE 2

To a solution of 1 part of 3β-hydroxy-25-methylcholest-5-en-7-one 3-acetate in 32 parts of ethanol is added 8 parts of an aqueous 5% sodium bicarbonate solution. The resultant mixture is heated at the boiling point for 3 hours, then cooled and thereupon neutralized with acetic acid. To the mixture thus obtained, 100 parts of water is added. The yellow precipitate which forms is isolated by filtration and chromatographed on neutral silica gel, using mixtures of benzene with increasing amounts of ethyl acetate as developing solvents. From an eluate comprising 25% ethyl acetate in benzene, on evaporation of solvent and recrystallization of the residue from aqueous ethanol, 3β-hydroxy-25-methylcholest-5-en-7-one melting at 176°–178° is obtained. The product has the formula

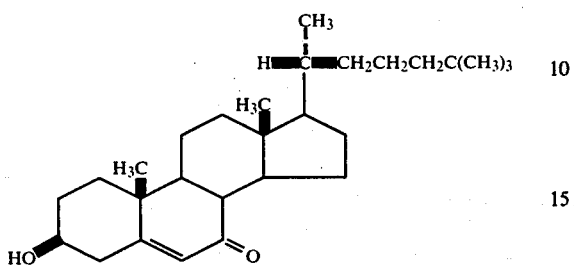

EXAMPLE 3

A. To a solution of 4 parts of 3β-hydroxy-25-methylcholest-5-en-7-one in 25 parts of pyridine is added a solution of 2 parts of 3-methoxy-3-oxopropanoyl chloride in 5 parts of pyridine. The resultant mixture is stirred at 90°–95° for 3 hours, then diluted with an equal volume of water. The mixture thus obtained is extracted with 1,1′-oxybisethane; and the extract is consecutively washed with 5% hydrochloric acid and water, then stripped of solvent by vacuum distillation. The residue is 3β-hydroxy-25-methylcholest-5-en-7-one 3-(3-methoxy-3-oxopropanoate).

B. A mixture of 4 parts of 3β-hydroxy-25-methylcholest-5-en-7-one 3-(3-methoxy-3-oxopropanoate), 12 parts of lithium iodide, and 30 parts of 2,6-dimethylpyridine is heated at the boiling point under reflux with stirring overnight, whereupon an equal volume of water is added and the solid precipitate which eventuates is filtered off, washed with water, and dried in air. The product thus isolated is 3β-hydroxy-25-methylcholest-5-en-7-one 3-(3-hydrogen propanedioate). The product has the formula

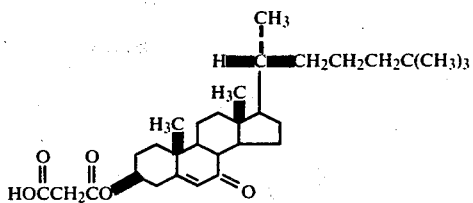

EXAMPLE 4

To a solution of 2 parts of 3β-hydroxy-25-methylcholest-5-en-7-one in 60 parts of pyridine is added 5 parts of butanedioic acid anhydride. The resultant mixture is heated at 90°–95° for 18 hours and then diluted with 10 volumes of water. A slight excess of 5% hydrochloric acid is introduced, and the resultant mixture is extracted with 1,1′-oxybisethane. The extract is consecutively washed with 5% hydrochloric acid and an aqueous saturated solution of sodium chloride; dried over anhydrous sodium sulfate; and stripped of solvent by vacuum distillation. The residue is crystallized from methanol to give 3β-hydroxy-25-methylcholest-5-en-7-one 3-(hydrogen butanedioate) melting at approximately 211°–212°. The product has the formula

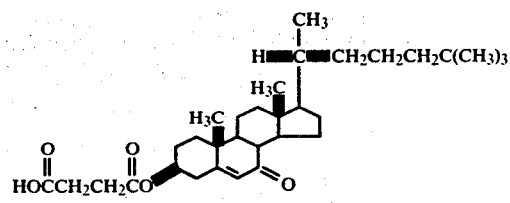

What is claimed is:
1. A compound having the formula

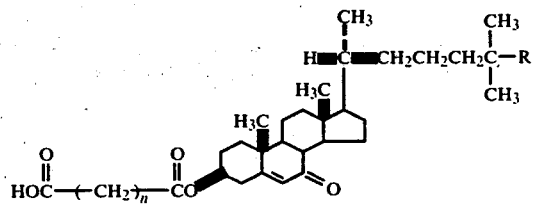

wherein n represents a positive integer less than 4 and R represents alkyl containing fewer than 5 carbons.

2. A compound according to claim 1 which is 3β-hydroxy-25-methylcholest-5-en-7-one 3-(hydrogen butanedioate).

* * * * *